United States Patent [19]

Arnold, Jr. et al.

[11] Patent Number: 4,950,613
[45] Date of Patent: Aug. 21, 1990

[54] PROTETED CHEMILUMINESCENT LABELS

[75] Inventors: Lyle J. Arnold, Jr.; Alexander A. Waldrop, III; Philip W. Hammond, all of San Diego, Calif.

[73] Assignee: Gen-Probe Incorporated, San Diego, Calif.

[21] Appl. No.: 160,611

[22] Filed: Feb. 26, 1988

[51] Int. Cl.$^5$ ............ G01N 33/533; G01N 33/532; C07D 265/38; C07D 295/00

[52] U.S. Cl. ............ 436/546; 436/544; 436/501; 546/102; 546/103; 546/104; 546/110; 546/169; 546/170

[58] Field of Search ............ 436/546, 544; 546/102, 546/103, 104, 110, 169, 170

[56] References Cited

U.S. PATENT DOCUMENTS 4,372,745  2/1983  Mandle et al. ............ 436/537
4,745,181  5/1988  Law et al. ............ 530/387

FOREIGN PATENT DOCUMENTS 2112779B  12/1982  United Kingdom .

OTHER PUBLICATIONS

McCapra, "Proposal in Organic Chemistry", vol. 8, pp. 231-277 (1973).
Weeks, et al., Clin. Chem., 29/8, pp. 1474-1479 (1983).
McCapra, "Accounts of Chemical Research", vol. 9, No. 6, pp. 201-208 (Jun. 1976).
Colowick et al., J. Biol. Chem., vol. 191, p. 447 (1951).
Ludwieg, et al. Biochem. Biophys. Res. Commun. vol. 14, p. 431 (1964).
"Acridines", Publs. John Wiley & Sons, Inc., London, U.K. (1973, ed., R. M. Acheson).

*Primary Examiner*—Christine M. Nucker
*Assistant Examiner*—Karen I. Kryper
*Attorney, Agent, or Firm*—Lyon & Lyon

[57] ABSTRACT

A method of preparing a labelled specific binding partner, such as a biological probe in the form of an antibody or oligonucleotide probe, using a protected label (the corresponding unprotected label being susceptible to inactivation, such as by hydrolysis to yield a non-chemiluminescent form of the label). The specific binding partner is linked to the label, and an adduct of the label is prepared using a protective adduct former which produces a protected label which is less susceptible to inactivation. Particularly preferred labels are the acridiniums and acridans, most preferably the former having the general structure:

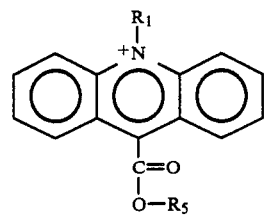

wherein the phenyl rings are optionally additionally substituted, $R_1$ is preferably an alkyl, and $R_5$ is an optionally substituted hydrocarbon, most preferably a phenyl moiety which is either linked to the specific binding partner, or capable of being linked thereto. Formation of the protected label is preferably an equilibrium reaction which is readily reversible, such as by dilution or oxidation of the protective adduct former. Labels useful in such a method are also disclosed.

32 Claims, 3 Drawing Sheets

PROTETED CHEMILUMINESCENT LABELS

FIELD OF THE INVENTION

The present invention relates to specific binding partners, such as biological probes, labelled with a protected chemiluminescent label, so as to inhibit label inactivation, and from which the deprotected, chemiluminescent label can be recovered.

TECHNOLOGY REVIEW

In clinical research and diagnosis, a known technique for determining the presence of a biological moiety, either qualitatively or quantitatively, involves using a probe which will link specifically with the moiety of interest (its specific binding partner). For example, in situations where an assay is to be performed for a target in the form of an antigen or a particular nucleotide sequence, the probe could be an antibody or an oligonucleotide, respectively. In any event, the probe is typically labelled, that is it is provided with an atom or a group linked thereto, the presence of which can be readily detected. To determine the presence of the target in a test sample, the labelled probe is exposed to the sample under conditions which will allow the labelled probe to link to its specific binding partner within the test sample (e.g., in the case of antibody probe, to bind with the antigen; in the case of oligonucleotide probe, to hybridize with the nucleotide multimer). Following this, any labelled probe/target complex present is typically separated from uncomplexed probe, and the presence of label determined in either the complexed or noncomplexed probe.

Historically, radioactive labels have been used. However, due to difficulties in handling, health hazards and instability, non-isotopic labels were later developed. Such labels include those whose presence is determined either directly or indirectly. Examples of direct labels include chemiluminescent, phosphorescent, fluorescent or spectroscopically detectable labels. Examples of indirect labels include compounds such as biotin and various antigens, which can be detected by means of specific binding partners conjugated to an appropriate detectable label. Of the foregoing label types, chemiluminescent labels, have been found to be particularly useful.

A number of chemiluminescent compounds are known. Some of these are reviewed by McCapra, Progress In Organic Chemistry, 8, 78(23), pp. 231–277 (1973). The foregoing reference, as are all other cited references, are incorporated herein by reference. Many of the foregoing compounds chemiluminesce upon treatment with hydrogen peroxide or oxygen, and hydroxide. Such compounds include acridiniums and acridans, having the structures I and II respectively, below, as well as compounds of the type of structure III, IV, and V below:

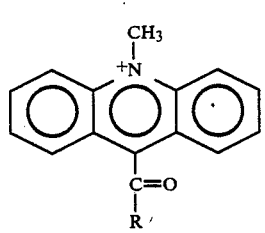
(I)

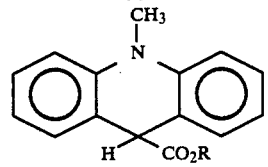
(II)

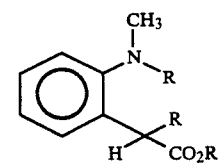
(III)

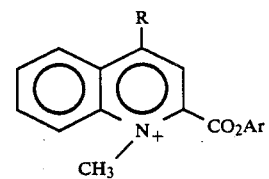
(IV)

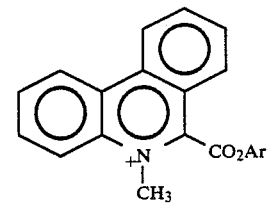
(V)

United Kingdom Patent No. 2 112 779B to Campbell et al. (Application No. 8235019; filed Dec. 8, 1982), discloses the use of acridinium esters of structure VI below, as chemiluminescent biological probe labels:

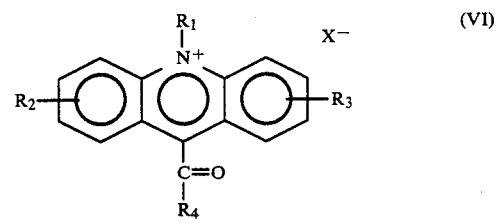
(VI)

In the above formula $X^-$ is any anion, $R_1$ represents H, $C_1$ to $C_{10}$ alkyl, alkenyl, alkynyl or aryl substituents; $R_2$ and $R_3$ are hydrogen, amino substituted amino, carboxyl, hydroxyl, alkoxyl, nitro, or halogen substituents; and $R_4$ is an optionally substituted phenoxy-moiety. Weeks, et al., Clin Chen. 29/8, pp 1474–1479 (1983) also discloses the use of acridinium esters of the above formula, as chemiluminescent antibody labels.

The chemiluminescent reaction mechanism for acridiniums and acridans, has been fairly well elucidated. In the case of acridiniums, the chemiluminescent reaction is initiated by the addition of hydrogen peroxide followed by base. As disclosed by McCapra, "Chemiluminescent Reactions of Acridines", Chemistry Of Heterocyclic Compounds, Volume 9, p. 16–30 (1973), the mechanism apparently involves peroxide attack upon the ring at the carbon 9 position, with subsequent deprotonation of the peroxide group and nucleophilic attack on the adjacent carbonyl to yield a dioxetane-like intermediate. This can occur simultaneously with cleavage of a leaving group, which may for example be an oxide anion (e.g., in the particular case of a acridinium phenyl ester, cleavage of phenoxide). It is known that the addition of hydrogen peroxide should occur prior to or simultaneous with base, since the acridinium exists in equilibrium with its corresponding "pseudo base" (represented by addition of hydroxide ion to the ring 9 position). The pseudo base is apparently not chemiluminescent, and to obtain rapid light emission from the acridinium, the pH should be low prior to hydrogen peroxide addition, so that the equilibrium of the acridinium and its pseudo base, is shifted in favor of free acridinium. An explanation of the foregoing is provided by Weeks et al, supra.

As pointed out by McCapra, "Chemiluminescence of Organic Compounds", Progress in Organic Chemistry, Vol. 8, 231-277 (1973), chemiluminescence of acridans would appear to first involve deprotonation of the acridan ring 9 position hydrogen in the presence of a strong base, to form the corresponding acridan anion, which reacts with oxygen at the ring 9 position, followed by subsequent dioxetane formation and oxide expulsion in a similar mechanism to that of acridiniums.

The chemiluminescent mechanism for acridiniums or acridans, would suggest that in either case, a good leaving group (e.g., phenoxide) is required. This requirement is borne out by McCapra, Accounts Of Chemical Research, Volume 9, No. 6, pp 201-208 (June, 1976), which discloses that the quantum yield (based upon chemical yield of excited product) increases with a decreasing pKa of ROH (where $RO^-$ is the leaving oxide anion). That is, quantum yield increases when $RO^-$ is a better leaving group.

Labelled probes are frequently prepared as a component of an assay test kit for a biological target. Typically, the kits contain labelled probe in the form of an aqueous solution. The difficulty with this situation is that chemiluminescent compounds of the above type are subject to hydrolysis at the ring 9 moiety (their active moiety) required for chemiluminescence. For example, in the case of acridinium phenyl esters, the carbonyl carbon of the ester "active moiety", is subject to hydrolysis even under slightly acidic conditions (eg. pH 6), to yield the non-chemiluminescent corresponding acridinium acid, and the leaving group (which in this case is the phenoxide anion). Such hydrolysis may occur when a probe bearing the label is used in an assay for a target. This is particularly the case where the probe is an oligonucleotide which is required by the assay protocol, to hybridize with a target sequence at elevated temperatures (eg., 60° C.) and over prolonged periods of time (eg. 2 hours).

With regard to pyridine analogues and acridine analogues, work has been done in a general manner relating to nucleophilic addition at the C4 and C9 positions, respectively. For example, such work is described in Colowick et al, J. Biol. Chem., Vol. 191, p. 447 (1951); Ludowieg et al, Biochem. Biophys Res. Commun., Vol. 14, p. 431 (1964); and in the text by Acheson, "Acridines", published by John Wiley and Sons Inc., London, U.K. (1973).

DEFINITIONS rlu - relative light unit. When a photon strikes the photomultiplier tube of a luminometer it starts an electronic cascade which results in a machine assigned number value. The efficiency of this process is machine dependent and the units therefore called relative light units.

adduct - refers to a single molecular product which results from the reaction of two structurally different reactants.

specific binding partner - a biological molecule which binds to another biological molecule with a high degree of specificity. For example each of an antibody and an analyte to which it specifically binds, is a specific binding partner (sometimes referred to as a "complement") of the other.

active moiety - a moiety of a chemiluminescent label which is in a state such as is necessary for subsequent excitation to the luminescent form.

Light-off - The specific reaction to produce chemiluminescence from a chemiluminescent label when desired.

light-off reagents - The reagents used to produce light-off of a chemiluminescent label.

inactivation - Any reaction which renders the chemiluminescent label unable to chemiluminesce at the time of light off.

adduct former - any chemical compound which is sufficiently reactive to form an adduct with another compound.

protective adduct formers - an adduct former which will protect a chemiluminescent label from inactivation.

SUMMARY OF THE INVENTION

The present invention is based upon a recognition that in order to obtain the maximum quantum yield from chemiluminescent labels of the type described above, the active moiety should have a good leaving group. However, this implies that the active moiety will be more sensitive to inactivation, since the carbon to which the leaving group is attached will be more sensitive to undesired reactions, such as hydrolysis or premature chemiluminescence. Thus, those labels of the above described type, which would produce the highest quantum yield, and hence could be used to provide labelled probes with high sensitivity, are also those which are most sensitive to inactivation. Label hydrolysis is a particularly problematic form of label inactivation. Label inactivation results in loss of assay sensitivity and accuracy, particularly during storage of kits containing labelled probes, or during an assay procedure which may promote label inactivation (e.g., hybridization of a labelled nucleotide probe with its specific binding partner, which in this case is a target nucleotide sequence). The present invention provides a means by which sensitivity of the label to inactivation can be reduced, thereby leading to improved label shelf life and increased assay sensitivity and accuracy. Broadly, this is accomplished by preparing adducts of the labels, with suitable protective adduct formers, which protect the active moiety from inactivation while readily permitting a chemiluminescent form of the label to be recovered from the adducts, typically following a complex formation with the biological target.

A method of preparing a labelled specific binding partner is provided, which method uses a peptide or nucleotide moiety, or other specific binding partner, and a chemiluminescent label. The label has an active moiety necessary for chemiluminescence but which is subject to inactivation to yield a non-chemiluminescent form of the label. The method comprises linking the specific binding partner to the label, and preparing an adduct of the label with a protective adduct former so as to provide a protecting moiety for the active moiety, and thus protect the active moiety from inactivation.

The adduct can either be prepared before or after the label is linked to the probe. However, if prepared after the label has been linked to the probe, it will be appreciated that it becomes more desireable to select conditions which are "non-adverse" to the probe (that is which do not result in a substantial proportion of the probe becoming ineffective to detect the specific binding partner for which it was intended). In the case of chemiluminescent compounds which chemiluminesce following treatment by hydrogen peroxide or oxygen and base, this will mean that the protecting moiety is other than OH or peroxide (OOH). Hydroxide is not considered a protecting moiety, since preparation and storage of an adduct from it requires solutions which are sufficiently alkaline to promote rapid hydrolysis of the active group. H can be used as a protecting moiety but is not preferred since the formation of compounds such as acridans requires reduction with hydride, a reaction which is not readily reversible. Peroxide on the other hand, is unsuitable as a protecting moiety for most chemiluminescent labels, since its presence will promote premature chemiluminescence. The protecting moiety is also selected such that the adduct can be deprotected to yield a chemiluminescent form of the label.

Preferably, the protective adduct former provides a protecting moiety by a readily reversible reaction. (most preferably a readily reversible equilibrium reaction), such that the protecting moiety is simply cleaved during deprotection to recover the chemiluminescent label.

Labels which might be used in the above method, have the following formula:

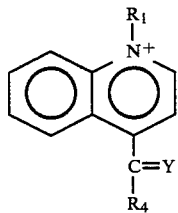
(VIa)

In the above formula, the pyridinium ring is optionally further substituted, and:
Y is O; S; or NH;
$R_1$ is an optionally substituted hydrocarbon or H;
$R_4$ is a leaving group;

is the active moiety which is linked to the ortho or para pyridinium positions, and is subject to hydrolysis to yield a non-chemiluminescent form of the label and the leaving group.

In such case, the protecting group is an adduct of a nucleophile at the a carbon in relation to the active moiety, that is in the case of structure VI above, a carbon of the pyridinium ring. Preferably the label is an acridinium compound of the formula:

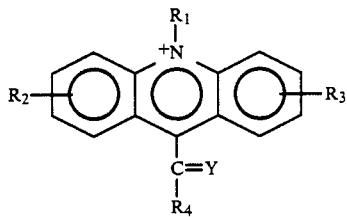
(VII)

in which $R_1$ is preferably an optionally substituted alkyl, akenyl, or alkynyl.

$R_2$ and $R_3$ are optional substituents, preferably selected from H, amino, hydroxy, thiol, halogen, amido, acetyl, alkyl, alkenyl, aryl substituted acetyl, substituted alkyl, substituted alkenyl, substituted acetyl, substituted alkyl, substituted alkenyl, substituted aryl, alkoxy, or aryloxy. $R_4$ may be halogen, substituted phosphorous, substituted nitrogen, substituted boron, substituted arsenic. $R_4$ may also be of the structure $-Z(R_5)(R_6)$ in which Z is O,S,N and $R_5$ is an optionally substituted hydrocarbon. In the foregoing $R_6$ is H or optionally substituted hydrocarbon if and only if $Z=N$.

Most preferably, the label is an acridinium ester of the formula:

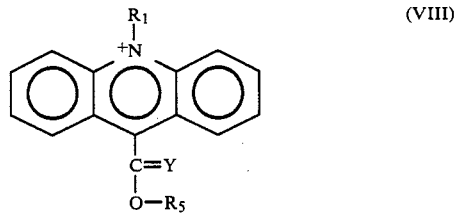
(VIII)

Various possible protective adduct formers can of course be selected, however it is preferred that the protective adduct former be a nucleophile selected from a primary thiol, most preferably from a primary alkyl or aryl thiol.

The present invention also provides protected chemiluminescent labels which are useful as biological probe labels as described below. In the following formulae,

is an active moiety of the type already described in connection with the method above, while M is a protecting moiety other than H or OH, or OOH (peroxide). The protecting moiety is cleavable to yield deprotected, chemiluminescent label, and is selected such that the C=Y carbon of the protected label is less susceptible to hydrolysis than in the deprotected label. $R_4$ (the leaving group) preferably contains a functional group which can be readily linked to a biological probe, or may already be linked to the probe.

Preferably, the protected labels have either the formula of IXb or IXc below:

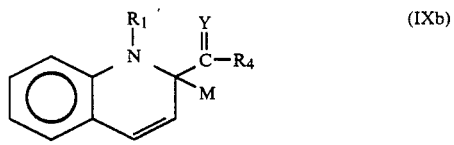
(IXb)

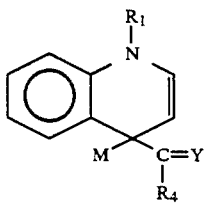

Protected chemiluminescent labels of the type IXb or IXc above, may be regarded as an adduct of a protective adduct former containing M, with labels of structure VI above, M⁻ being added to the a carbon in relation to the active group. The most preferable of the protected labels, are the acridinium esters of the following formula:

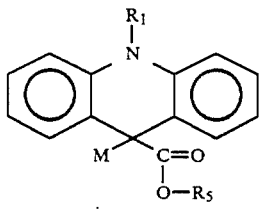

In which the M is preferably a primary thiol.

The present invention further provides biological probes linked to protected labels of the above described type.

DRAWINGS

Embodiments of the invention will now be described with reference to the drawings, in which:

FIG. 1: is a graph illustrating stability of protected labels of the present invention over time (see Example 1);

FIG. 2: is a partial ultraviolet spectrum illustrating the dependence of protection offered to labels by protective adduct formers, upon protective adduct former concentration (see Example 2);

FIG. 3: is a graph illustrating dependence of formation of adducts of the present invention, on protective adduct former concentration (see Example 3);

FIG. 4: illustrates a readily reversible equilibrium reaction for formation of a particular protected label of the present invention (see Example 4);

FIG. 5: is a graph illustrating recovery of signal, and hence recovery of deprotected label, from protected label of the present invention by means of oxidation of the adduct former (see Example 6);

FIG. 6: illustrates temperature stability of adducts of the present invention (see Example 8);

DETAILED DESCRIPTION OF EMBODIMENTS OF THE INVENTION

Figure 6:
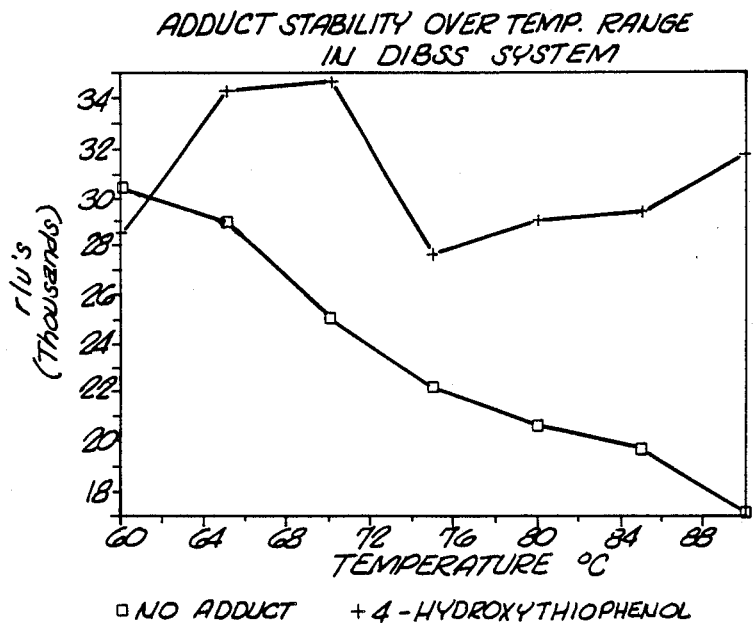

A procedure for selecting suitable protective adduct formers for producing protected labels of the present invention, will first be described. Also described is a procedure for linking specific binding partners with the labels. Next is illustrated the dependence of protection of protected labels of the present invention, from peroxide inactivation, on adduct former concentration. The next examples are devoted to novel ways of reverting protected labels of the present invention, to the unprotected label through (1) dilution (2) general oxidation (3) specific oxidation. Following this, the utility of protective adduct formers in manipulation of acridinium esters, is shown.

In the case of acridinium ester labels of formula VII above, protection of the active moiety, in particular the C=Y (e.g., carbonyl) carbon thereof, from hydrolysis can be obtained by making an adduct between a suitable nucleophile and the label, such adduct being formed at the a carbon in relation to the active group (i.e., specifically this will be a pyridinium ring carbon). Potentially suitable protective adduct formers can be ascertained in this case, by experimentally determining their ability to decrease hydrolysis of the active moiety. Such a technique is illustrated in Example 1 below.

EXAMPLE 1

Method of selecting protective adduct formers.

Various nucleophiles were selected as potential protecting groups for acridinium phenyl ester having the formula:

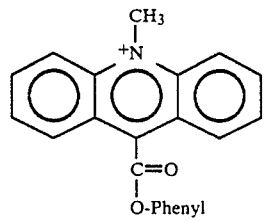

The ability of each nucleophile to act as a protecting moiety was experimentally ascertained by mixing the nucleophile (in the form of a potential adduct former listed as "Agent" Table 4 below) in the following aqueous test solution:

0.5 M phosphate buffer ("PB")—pH 6.0
0.1% sodium dodecyl sulfate ("SDS")
5 mM of the agent
$10^6$ rlu of a biological probe in the form of a 26 base pair ("bp") oligonucleotide, labelled with substituted acridinium phenyl ester.

Labelling of the oligonucleotide probe can be accomplished by means of the method described in pending U.S. patent application entitled "Acridinium Ester Labeling and Purification of Nucleotide Probes", filed Oct. 5, 1987, Ser. No. 105,080.

The above mixture was incubated at room temperature for 30 minutes followed by incubation at 60° C. and an aliquot extracted at times indicated in Table 1 below. The aliquot was then added to 100 microliters ("μl") of 0.5 N HNO₃ to insure that any pseudo base form of the acridinium ester present was converted to the free ester. Light off was then accomplished by adding to the nitric acid solution, 100 μl of 0.2% $H_2O_2$ followed by 200 μul of alkaline phosphate buffer (pH 12.75). Light emission measurements were also made on a number of controls, consisting of the above mixture absent the potential adduct forming compound being tested (i.e., the "Agent"). Light emission was measured over approximately 10 seconds in each case, and the resulting value at each time (in thousands of rlu's) is listed below in Table 1. The nucleophilic component of the agents tested were considered to be potentially suitable protective adduct formers if light emission was significantly greater at each time point following zero minutes, than in the control. Based upon the foregoing criterion, an indication of those adducts formers considered to produce protected labels of the present invention and which are potentially suitable in the method of the present invention, are indicated with a "Y" under the column entitled "Potentially Suitable" in Table 1 below:

TABLE 1

| Agent | Time (minutes) | | | | | Potentially Suitable (Y/N) |
|---|---|---|---|---|---|---|
| | [R.T.] | | [60° C.] | | | |
| | 0 | 30 | 15 | 30 | 60 | |
| control | 72 | 63 | 24 | 11 | 2 | — |
| Sodium Bisulfite | 76 | 76 | 68 | 73 | 51 | Y |
| Sodium Isothiocyanate | 73 | 69 | 34 | 16 | 3 | N |
| Thiourea | 73 | 70 | 30 | 12 | 2 | N |
| Mercaptoethanol | 40 | 40 | 31 | 27 | 18 | Y |
| Dithiothreitol | 39 | 36 | 31 | 26 | 18 | Y |
| Hydroxylamine | 77 | 81 | 42 | 22 | 8 | Y |
| N,N-dimethylhydroxylamine | 76 | 84 | 30 | 12 | 2 | N |
| N-Bromosuccinimide | 39 | 17 | 0.2 | 0.2 | 0.2 | N |
| N-iodosuccinimide | 69 | 40 | 3 | 0.9 | 0.4 | N |
| N-hydroxysuccinimide | 71 | 68 | 31 | 15 | — | N |
| Periodate | 65 | 66 | 27 | 10 | 2 | N |
| Hydrogen Peroxide | 67 | 69 | 31 | 13 | — | N |
| Imidazole | 71 | 75 | 28 | 13 | — | N |
| Hypochlorite | 2 | 0.2 | 0.4 | 0.2 | — | N |
| Anline | 68 | 56 | 29 | 13 | — | N |
| Azide | 69 | 67 | 29 | 13 | — | N |
| Ethylene diamine | 87 | 80 | 34 | 17 | — | N |
| Hydrazine | 76 | 69 | 31 | 14 | — | N |
| Control | 41 | 42 | 20 | 8 | 1.7 | — |
| 2,5-dimercapto-1,3,4-thiadiazole | 46 | 42 | 23 | 14 | 10 | Y |
| Cysteamine | 37 | 33 | 16 | 6.5 | 1.6 | N |
| 4-hydroxythiophenol | 6 | 5 | 8 | 11 | 32 | Y |
| Sodium cyanide | 41 | 39 | 17 | 6 | 1.4 | N |
| Thiol acetic acid | 38 | 40 | 18 | 8 | 2 | N |
| Sodium thiophosphate | 38 | 32 | 16 | 9.5 | 4.4 | N |
| Control | 175 | — | 70 | 53 | *63 | — |
| 4-aminothiophenol | 30 | — | 65 | 64 | *70 | Y |
| 3-mercaptopropionic acid | 77 | — | 67 | 69 | *76 | Y |
| Thiosalycylic acid | 127 | — | 67 | 58 | *62 | N |
| Mercaptoethanesulfonic acid | 131 | — | 63 | 71 | *71 | Y |
| Sodium hydrosulfite | 153 | — | 71 | 86 | *118 | Y |
| Mercaptosuccinic acid | 153 | — | 66 | 64 | *77 | N |
| Control | 509 | — | 319 | 245 | 143 | — |
| Cysteine | 334 | — | 280 | 283 | 227 | Y |
| 2-Aminoethanethiol | 421 | — | 349 | 334 | 261 | Y |

Figure 1:
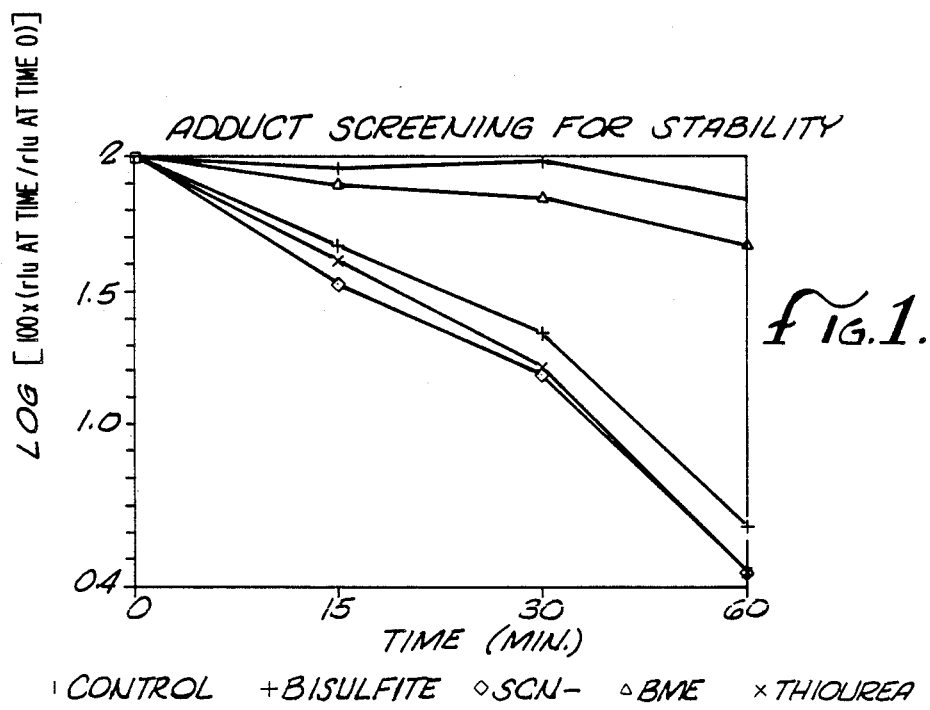

*These readings taken at 45 minutes rather than 60 minutes. (Numbers are in 1,000's of rlu's)
R.T. = room temperature The results for some of the potential adduct formers listed in Table 1, are illustrated in FIG. 1, as a plot of:

Log[100 ×(rlu at time)/(rlu at time 0)]

versus time. As will be seen from both Table 1 and FIG. 1, many of the agents tested provided protecting moieties which decreased label inactivation. Those adduct formers are indicated with a "Y" in Table 1 above, under the column titled "potentially suitable".

The protection provided by protecting moieties of the agents which are potentially suitable adduct formers, conveys two potential advantages in particular. First, the shelf life of specific binding partners labelled with protected labels is greater than that of probes labelled with corresponding unprotected label. Second, such protection is particularly beneficial during complex formation of the labeled specific binding partner with its complement, under harsh conditions which might promote hydrolysis of the label. For example, when the specific binding partner is an oligonucleotide probe which is to be hybridized with a complement target during the assay, at elevated temperatures and over an extended time period. As shown in Table 1 and FIG. 1, an elevated temperature of 60° C. considerably increases the rate at which the unprotected label is inactivated, apparently being hydrolyzed to a non-chemiluminescent form. It will also be seen from Table 1 and FIG. 1, that initial light emission from protected label is in many cases, considerably lower than from the corresponding unprotected label. This is apparently the result of the adduct forming a strong link with the label in competition with hydrogen peroxide during light off. As will be seen below, these apparently "lost rlu's" of light emission, are recoverable by techniques which will be described.

It should be borne in mind that whether any potentially suitable protective adduct former is in fact suitable in a given situation will depend upon the specific binding partner with which the label will be used. For example, it has been found that where the specific binding partner is an oligonucleotide probe, the use of bisulfite decreases hybridization markedly. This is likely due to resulting decomposition of cytosine to uridine, thereby reducing homology between the probe and its target (i.e. its complement). Thus in a particular case one should check for adverse effects of a potentially suitable protective adduct former, on the specific binding partners with which it will be used.

EXAMPLE 2

Concentration Dependence of Protection From Peroxide

This example illustrates the dependence of formation of protected labels of the present invention, on adduct former concentration. Five solutions were prepared each containing the following:

0.5M phosphate buffer at pH 6.0;
0.1% SDS;
80 nanomolar ("nM") of acridinium phenyl ester label; ever increasing amounts of the adduct former 3-Mercaptopropionic acid ("MPA") were added to achieve concentrations from 0 to 10 mM.

Figure 2:
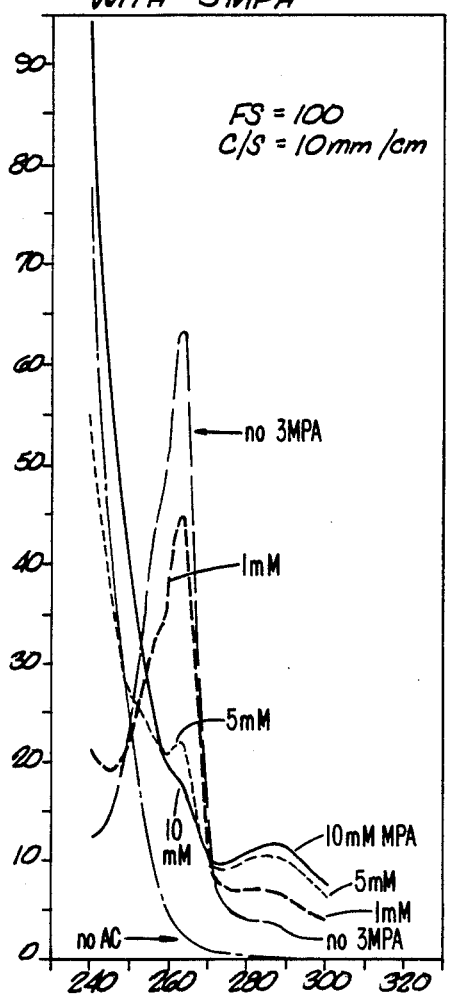

Ultraviolet ("UV") scans of the resulting mixtures were then obtained in the region 300–240 nanometers ("nm"), these scans being illustrated in FIG. 2.

The absorption at 260 nm corresponds to the non-adduct acridinium ring structure. Thus, as is seen from FIG. 1, increased concentrations of the adduct former cause a corresponding decrease in the 260 nm absorption due to conversion of the acridinium ring structure to an adduct. It was also observed that the amount of adduct did not change significantly with time at a fixed concentration of MPA. This indicates that the adduct is in dynamic equilibrium with the free acridinium structure.

EXAMPLE 3

Concentration dependence of protection from peroxide as seen by chemiluminescence.

This example also illustrates that as in Example 2, the extent of formation of protected label is dependent upon adduct former concentration.

Figure 3:
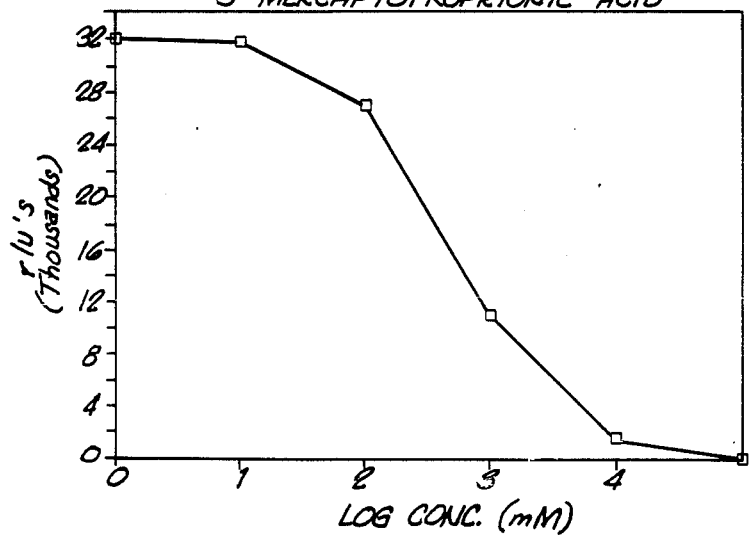

In this example, various solutions of the following composition were prepared by adding 1 μl of a solution containing the acridinium ester labelled probe, to 100 μl of 0.5 N $HNO_3$ followed by the required amount of adduct former (3-Mercaptopropionic acid) to produce adduct former concentrations indicated in FIG. 3. Light off was then accomplished by adding to each resulting mixture 100μl of 0.2% $H_2O_2$ (by weight-volume) followed by addition of 200 μl of alkaline phosphate buffer pH 12.75. The resulting light emission versus a log of the concentration of adduct former (in mM) is plotted in FIG. 3.

FIG. 3 also illustrates the dependence of the formation of some of the protected labels of the present invention, upon the concentration of adduct former. That is, the higher the concentration of adduct former the higher will be the proportion of label converted to the protected label form. This result also suggests that at least with the adduct formers of the present example, the chemiluminescent label can be recovered from its non-chemiluminescent protected form, by reducing adduct former concentration.

EXAMPLE 4

Demonstration of reversibility through dilution.

One means of reducing adduct former concentration, in order to recover the chemiluminescent label, is simply to dilute a solution containing the label and adduct former. This technique of course, will only be effective providing that a solution is chosen wherein the overall chemical solution is such that dilution will cause a shift in the equilibrium reaction between the adduct former and label to produce the protective label. In considering a primary thiol adduct former, the expected equilibrium reaction would be:

$$RSH + Acr^+ \rightleftharpoons H^+ + RSAcr \quad (1)$$

In the above, RSH is the adduct former in the form of a primary thiol, $Acr^+$ is the unprotected acridinium ester label, and RSAcr is the acridinium adduct (i.e. protected label). In such a system, when a buffer is present $H^+$ concentration remains constant, such that dilution of the solution results in a shift of the equilibrium to the left, with the consequent deprotection of the protected acridinium ester label to recover the chemiluminescent acridinium ester label.

Figure 4:
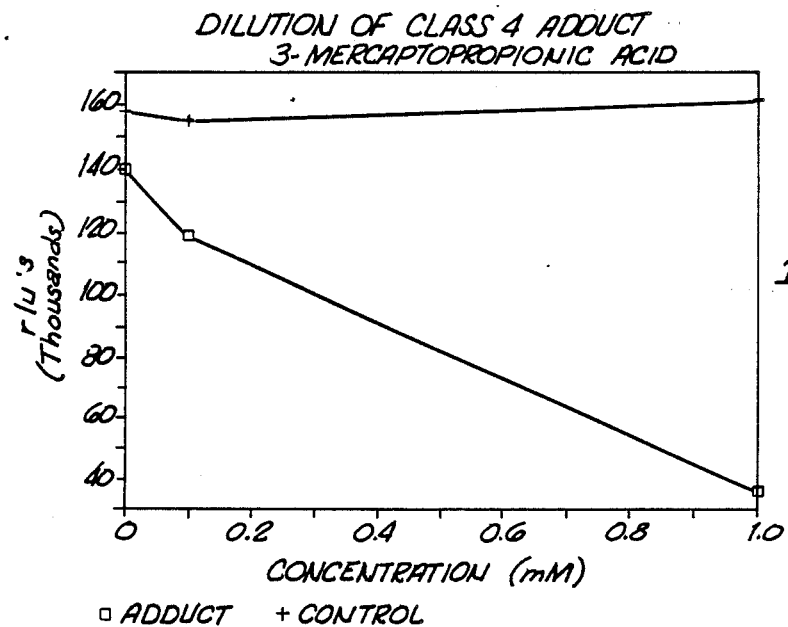

To illustrate this, a trial solution was prepared by adding to acridinium phenyl ester in a phosphate buffer solution (pH 6.0), a solution of the adduct former 3-mercaptopropionic acid to bring the final adduct former concentration to 10 mM. This solution was then diluted to prepare resultant trial samples containing various concentrations of the adduct former which are indicated in FIG. 4. Light off of these trial samples was then accomplished by adding to the diluted samples 100 μl of 0.5 N $HNO_3$, followed by 100 μl of 0.2% $H_2O_2$ then 200 μl of alkaline phosphate buffer pH 12.75. Light emission, corrected for the dilution used, versus concentration is plotted in FIG. 4 both for the trial samples, as well as for control samples prepared in accordance with the same technique except without any protective adduct former present.

It is apparent from FIG. 4 that for the protective adduct former 3-mercaptopropionic acid, the equilibrium reaction of equation (1) above, is a readily reversible equilibrium reaction. In particular, with this adduct former the chemiluminescent label is readily recoverable by procedures which shift the equilibrium in favor of deprotection of the protected label, for example by dilution under substantially constant pH.

Example 5

Reversion by washing after binding to a solid support.

In the case where the specific binding partner is an oligonucleotide probe labeled with a protected label of the present invention, and the resulting probe/target hybrids are bound to a solid support, the dilution described in Example 4 above can readily be accomplished during washing of the support following hybridization. This is illustrated by the present example. "Labelled probe hybrids" were prepared and treated using the following procedure:

(i) a hybrid was preformed in phosphate buffer ("PB"), pH 6.0, between a 26 bp oligonucleotide labeled with acridinium phenyl ester, and a target nucleotide sequence;

(ii) hybridized, labelled probe was separated from non-hybridized probe on a solid support, and the solid support then washed with PB, pH 6.0;

(iii) 50 μl of the slurry from step (ii) was treated with nitric acid and lit off in the same manner as described in connection with Example 4; light emission is recorded in Table 2 under "Pre-adduct" (all Table 2 light emissions are listed in rlu's);

(iv) to the remainder of the slurry supply from step (ii), sufficient 3-mercaptopropionic acid (protective adduct former) was added, to bring its concentration to 10 mM;

(v) another 50 ul aliquot of the slurry from step (iv) was then lit off in the same manner as in step (iii), and emission recorded under "After Formation" in Table 2 below;

(vi) the remainder of the resulting slurry from step (iv) was washed once with PB and a 50 ul aliquot lit off using the procedure of step (iii) above; the resulting emission is recorded in Table 2 under "After Wash One".

(vii) The remainder of the slurry resulting from step (vi) was washed again with PB, and another aliquot then lit off using the procedure of step (ii) above; the emission is recorded under "After Wash Two" in Table 2 below.

The above procedure was also repeated with a control and a blank, in the case of the control no protective adduct former (i.e., no 3-mercaptopropionic acid) was added, and in the case of the blank there was no oligonucleotide. The light emission from each of the control and blank are listed in Table 2 below, along the lines labeled "Control" and "Blank", respectively.

TABLE 2

|  | Pre-Adduct | After Formation | After Wash 1 | After Wash 2 |
|---|---|---|---|---|
| Labelled Probe Hybrids | 15189 | 740 | 13739 | 13738 |
| Control | 14896 | 12093 | 15020 | 11779 |
| Blank | 588 | 616 | 647 | 573 |

As is apparent from Table 2, the MPA effectively converted almost all of the label to a protected, non-chemiluminescent label, as illustrated by the light emission under the column "after formation". Further, deprotection was readily accomplished by washing with PB, to yield the unprotected, chemiluminescent label, with one wash being as effective as two washes. Of course, for the purpose of a clinical assay, a test kit would typically be prepared prior to the assay, which contained the unhybridized probe labelled with a protected label of the present invention, so as to minimize label inactivation, both during storage of the labelled probe and during incubation in the assay procedure. However, the same qualitative results given in Table 2 would be expected in this situation also.

Example 6

Reversion by oxidation with $Fe(CN)_6^{-3}$

Figure 5:
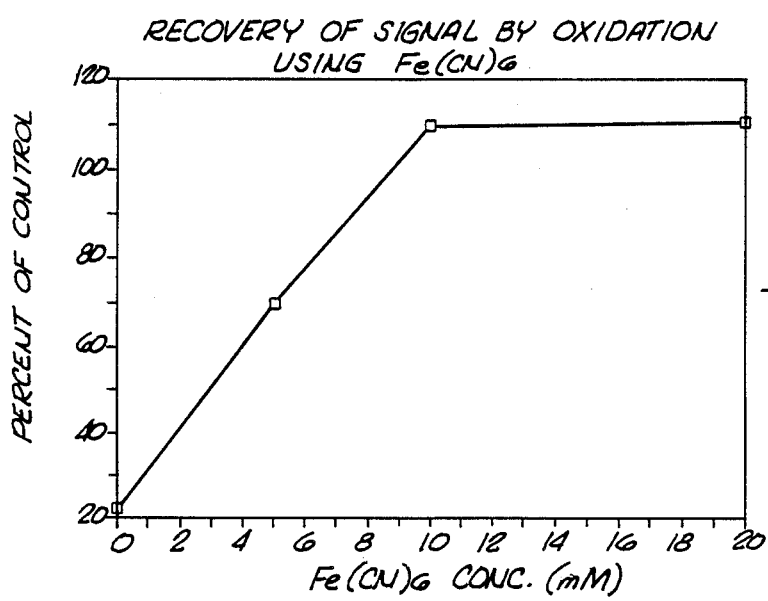

As has been illustrated in the above examples, the equilibrium reaction between those protective adduct formers and a label, such as an acridinium ester label, is readily reversible to recover the chemiluminescent, unprotected label. Dilution has been shown to be one way of shifting the equilibrium in favor of unprotected label, however, other methods of shifting the equilibrium will be apparent. The present example illustrates another such method, namely oxidation of the protective adduct former. In this example, the following procedure was followed:

(i) a 26-mer oligonucleotide probe, labelled with acridinium phenyl ester, was mixed in PB (pH 4.9);

(ii) a sufficient amount of the protective adduct former, 4-hydroxythiophenol, was added to bring its concentration to 7.5 mM;

(iii) 5 ul aliquots of the solution from (ii) preceding, were added to respective 5 ul aliquots of a potassium ferricyanide $<K_3Fe(CN)_6>$ solution of the concentrations indicated in FIG. 5, resulting in a number of trial samples;

(iv) each of the trial samples from step (iii) preceding, was then lit off according to the procedure described in connection with Example 1 that is by adding to nitric acid, followed by a treatment with hydrogen peroxide and then alkaline phosphate buffer pH 12.75.

The same procedure was repeated using a control, in which no adduct former (4-hydroxythiophenol) was added. The results of light emission from the trial samples are plotted in FIG. 5 as light emission in the form of the percent of emission from the sample in comparison to that of the corresponding control sample, versus ferricyanide concentration in the solution to which the labelled probe was added (the ferricyanide concentration in the resulting samples then, being one-half that indicated in FIG. 5).

As is seen in FIG. 5 oxidation of the adduct former 4-hydroxthiophenol is also a very effective way in which to shift the equilibrium to deprotect the protected label, and recover the unprotected chemiluminescent label. In a clinical assay such a deprotection step would typically follow complex formation between the labelled probe and target, prior to light off.

Example 7

Reversion of adducts by reaction with a thiol-specific reagent.

The reversion demonstrated above in Example 6 uses a nonspecific oxidizing agent. Here the use of a specific reagent is demonstrated. In this case Aldrithiol (2,2'-dithiodipyridine) is useful as an agent to reverse adduct formation, since the protective adduct former is a reactive primary thiol. This reactant is not inclusive of all possibilities and other thiolspecific reagents, or reagents specific for other protective adduct forming nucleophiles, can be used. The following procedure was used:

(i) Acridinium ester labelled oligonucleotide probe solution was prepared by adding probe to a solution of 50% formamide (by volume), 0.2M PB pH 6.0;

(ii) solutions of the adduct former 2-mercaptoethanesulfonic acid ("2MESA"), and solutions of aldrithiol, were each prepared at 0, 0.1, 1, and 10 mM in the above buffer and 100% formamide respectively;

(iii) to 100 ul of probe solution was added 100 ul of adduct solution and 100 ul of Aldrithiol solution as indicated in Table 3 below;

(iv) Samples so prepared were incubated 5 min at room temperature then light off was done by addition of 200 ul of 0.4N $HNO_3$ with 0.1% $H_2O_2$, followed by 200 ul of 1N NaOH.

The results in Table 3 below indicate that a stoichiometric reversion occurs by effectively reducing the concentration of adduct former in solution.

TABLE 3

|  |  | Conc of 2MESA (nM) | | | |
| --- | --- | --- | --- | --- | --- |
|  |  | 0 | 0.1 | 1 | 10 |
| Aldrithiol | 0 | 154204 | 148311 | 149732 | 155337 |
| Conc (nM) | 0.1 | 113118 | 120684 | 154596 | 160838 |
|  | 1 | 48633 | 81757 | 143273 | 161568 |
|  | 10 | 14925 | 20776 | 13499 | 130935 |

EXAMPLE 8

Decreased temperature sensitivity with the use of adducts.

To illustrate the temperature stability of protected labels of the present invention, two aqueous samples of the following solutions were prepared:

"DIBSS mix" (i.e., 45 weight percent diisobutyl sulfosuccinate <"DIBBS">, plus phosphate buffer, ethylenediaminetetraacetate <"EDTA"> and EGTA <ethyleneglycol-bis-(B-aminoethyl ether)-N,N,N',N'tetraacetic acid>mix pH 6.8); $10^6$ rlu of acridinium phenyl ester labelled 26 base pair ("bp") oligonucleotide.

Two DIBSS solutions were prepared, with 0 or 5 mM 4-hydroxythiophenol. 2 ul of probe in 3% LDS (lithium dodecyl sulfate) was added to 20 ul of either DIBSS mix. Each temperature point was done with an individual sample prepared as above. Samples were placed in a water bath for five minute incubations, at increasingly elevated temperatures. Light off of each aliquot was then accomplished using hydrogen peroxide followed by nitric acid treatment then base. Light emission versus temperature is plotted in FIG. 6, for the aliquots from the two samples.

As is seen in FIG. 6 the 4-hydroxythiophenol apparently produced an adduct of the acridinium ester, which was considerably more stable at elevated temperatures than the acridinium ester itself. Thus, protected labels of the present invention are particularly advantageous when the probe to which they are linked, is an oligonucleotide and it is desired to use elevated hybridization temperatures.

EXAMPLE 9

Improvement of signal recovery after long hybridization.

The effects of protecting a label linked to an oligonucleotide probe, during long term hybridizations, will now be illustrated. In this example, three trial solutions were prepared using the same mixture as in Example 8 with no protective adduct former being provided in one sample, 3-mercaptopropionic acid being provided in a second sample, and 4-hydroxythiophenol being provided in the third sample. Each of the protective adduct formers and the acridinium ester, would then form the corresponding protected labels. An aliquot from each of the foregoing solutions, was then hybridized with the same target nucleotide sequence rRNA, at 600° C. for 2.5 hours. Each sample was bound to hydroxyapatite and the supernatant removed as "nonbind", the support washed once with phosphate buffer and the washing saved as "wash". Light emission from support, nonbind, and wash was measured using the light off procedure of Example 5. Light emission is shown in Table 4.

TABLE 4

| SIGNAL RECOVERY AFTER 2.5 HOUR HYBRIDIZATION | | | |
|---|---|---|---|
| Protective | rlu's | | |
| Adduct Former | Support | Nonbind | Wash |
| none | 6450 | 5027 | 671 |
| 4-hydroxythiophenol | 21677 | 43692 | 3111 |
| 3-Mercaptopropionic acid | 23476 | 11160 | 1041 |

Note that the signal is almost 3 times greater in the samples protected with adducts than in the control sample. All trials had an amount of label which could yield the same rlu's.

The results of Table 4 then, illustrate the effect of providing a protecting group for oligonucleotide-linked acridinium ester label, on oligonucleotide/target hybridization, over long periods of time. As will be seen from Table 4, protected labels of the present invention allow greater signal recovery (i.e. they exhibit slower label inactivation) than is obtained with unprotected label, and hence allow for a target assay having increased sensitivity. This is particularly true for long incubation periods (eg. greater than about 2 hours).

Example 10

Improved Storage stability through the use of adducts.

Improved stability as demonstrated in the above examples has many benefits. Of particular interest is improved storage of an acridinium ester labelled probe. To illustrate this improved storage stability the following conditions were used. A solution was prepared as below:

0.1M Lithium Succinate pH 5.2
0.1% Lithium Lauryl Sulfate
Acridinium ester labelled DNA probe 10 mM 3-mercaptopropionic acid (not present in control sample)

This solution was assayed for chemiluminescent activity of the label by adding 5 ul of a one hundred fold dilution of the solution to 300 ul of 50% formamide, 0.2M Phosphate buffer pH 6.0, light off was achieved as in Example 7 above. 1 ml aliquots of the solution were then lyophilized and the resulting pellets incubated for 1 or 3 days at 45° C. They were then reconstituted to the original volume and assayed for retention of chemiluminescent activity, listed below as a percentage.

| | % of initial activity remaining | |
|---|---|---|
| Condition | Day 1 | Day 3 |
| No adduct | 61% | 23% |
| With adduct | 101% | 105% |

It is evident that a substantial degree of improved stability is gained when storage is done as the adduct. The elevated temperature condition used is a common way of estimating how good stability will be for longer periods at a lower temperature.

Summary of working examples

It will be seen from the above then, that a chemiluminescent label can be protected using various adduct formers to produce a protected label, which can be less susceptible to inactivation, such as by hydrolysis, than the unprotected label, due to the presence of the protecting moiety from the adduct former. It has also been shown above, that in many cases reaction of the protective adduct former with the label is an equilibrium reaction which can often be readily reversed by means such as dilution or oxidation of the adduct former. However, in the case of readily reversible equilibrium reactions of the foregoing type, it will be appreciated that many other means of shifting the equilibrium in favor of unprotected label, can be envisaged. For example, in the case of formation of a protected phenyl acridinium label using the adduct former 3-Mercaptopropionic acid equilibrium has been shifted in favor of deprotected label by adding N-ethylmaleimide, or 2,2'-dithiodipyridine. It will be apparent though, that various other adduct formers can be chosen for adding protecting groups to the label, and means for recovering the unprotected label formulated depending upon the particular adduct former. Furthermore, it will be appreciated that the present invention can be used to protect labels which are linked to specific binding partners other than oligonucleotide probes. The basic concept of the present invention, is to provide labels either already linked to specific binding partners, or which may be linked to them, which labels have an active moiety necessary for luminescence and which is subject to inactivation, which active moiety is protected by a protecting moiety such that the active moiety is less susceptible to inactivation than in the deprotected label, and which deprotected, chemiluminescent label can be recovered typically following an assay.

The above invention also has application to an assay in which the protective adduct former is provided linked to a specific binding partner in the assay system, rather than being provided essentially in a free form as in the above examples. This technique has the advantage that when a labelled specific binding partner complexes with a complement, which either itself may carry the protective adduct former or which may further complex with another complement which does carry the protective adduct former, the label can be protected. This in effect results from the local concentration of the protective adduct former near the label, being high. However, uncomplexed label will not be protected to the same extent and hence can be selectively inactivated.

The foregoing technique can be applied for example to a two site assay involving a total of 3 specific binding partners. One partner would carry the protective adduct former, while a second partner would carry the unprotected label. Such assays could include sandwich and sequential saturation type assays. However the technique also has application to a single site assay (involving only 2 specific binding partners).

In addition, in this technique, the assays may be either homogeneous or heterogeneous. Regardless of the assay type the underlying principle is that the local concentration of the adduct forming agent in the vicinity of a chemiluminescent label can be changed in relationship to the presence of the target to be detected.

As a particular example, the assay type could be a two site DNA probe assay whereby two DNA probes bind to adjacent sites on a common polynucleotide target. In such an assay the chemiluminescent label could be placed on the end of a first probe and the adduct forming agent could be positioned on the end of a second probe, such that when both probes bind to a target nucleotide sequence, the protective adduct former will be proximal to the chemiluminescent label on the first probe. The simultaneous binding of the two probes to the same target polynucleotide, would result in the concentration of the adduct forming agent then, increasing significantly in the vicinity of the chemiluminescent label. Such increased concentration, should in turn increase the stability of the complexed chemiluminescent label, making it possible to discriminate the complexed and uncomplexed forms of the probes based on their relative stabilities. After appropriate inactivation of the label on the uncomplexed chemiluminescent probe, by means of which does not substantially affect the protected probe, and reversion of the adduct associated with the complexed probe, the amount of intact chemiluminescent label would serve as a measure of the amount of said complex and thus as a measure of the amount of target present. The basic steps in such an assay are as follows:

1. Complex specific binding partners involved in the assay with one another, so that the local concentration of protective adduct former in the vicinity of label in complexed binding partner, will be high;
2. then inactivate unprotected label, such as by degradation (e.g., hydrolysis of acridiniums);
3. then deprotect protected label;
4. then detect the amount of intact label as a measure of target present.

As illustrated above this invention can be readily employed for the design of homogeneous assay types. However it may also be employed as an adjunct to heterogeneous and homogeneous assay formats where it is desirable to further discriminate complexed and uncomplexed specific binding partners.

Various modifications and alterations to the embodiments of the invention described above, can be envisaged by those skilled in the art. Accordingly, the present invention is not limited to the embodiments and modifications described in detail above.

We claim:
1. A method of preparing a labelled specific binding partner, from:
  (i) a specific binding
  (ii) a chemiluminescent label having a labile, active moiety which is subject to inactivation to yield a non-chemiluminescent form of the label;
the method comprising:
  (a) linking the specific binding partner to the label; then
  (b) preparing an adduct of a protective adduct former with the label so as to protect the active moiety from inactivation, from which adduct a chemiluminescent form of the label can be recovered.
2. A method of preparing a labelled specific binding partner, from:
  (i) a specific binding partner; and
  (ii) a chemiluminescent label having a labile, active moiety which is subject to inactivation to yield a non-chemiluminescent form of the label;
the method comprising:
  (a) linking the specific binding partner to the label;
  (b) preparing an adduct of a protective adduct former with the label, which adduct former provides a protecting moiety other than H to the label, so as to protect the active moiety from inactivation, and from which adduct a chemiluminescent form of the label can be recovered.

3. A method as defined in claim I wherein the label is of the formula:

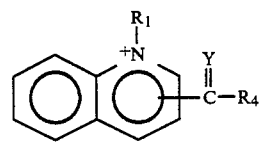

wherein:
  the pyridinium ring is substituted or unsubstituted further substituted;
  Y os O; S; or NH
  $R_1$ is a substituted or unsubstituted hydrocarbon or H;
  $R_4$ is a leaving group;

is an active moiety which is subject to hydrolysis to yield the label and the leaving group, and is linked to the ortho or para pyridinium ring positions; and
wherein the protective adduct former is a nucleophile which adds at the pyridinium carbon a in relation to the active moiety.

4. A method as defined in claim 3 wherein the label is an acridinium compound of the formula:

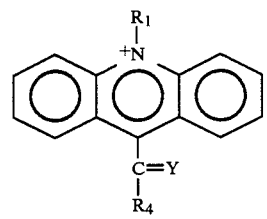

in which either pyridinium ring is optionally further substituted.

5. A method as defined in claim 4 wherein $R_1$ is an optionally substituted alkyl, alkenyl, or alkynyl.

6. A method of preparing a chemiluminescent specific binding partner from:
  (i) a specific binding partner;
  (ii) a chemiluminescent label of the formula:

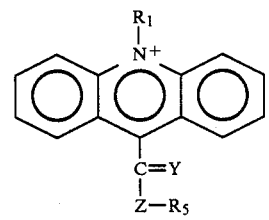

wherein:
  the phenyl rings are optionally substituted;
  $R_1$ = a substituted or unsubstituted hydrocarbon or H;
  Y = O; S; or N Z=O; N; halogen; substituted or unsubstituted S; substituted P; substituted B; or substituted As;

—Z —R$_5$ is a leaving group;

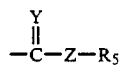

is an active moiety which is subject to hydrolysis at the C=Y carbon to yield a non-chemiluminescent hydrolyzed label and the leaving group;

R$_5$=optionally substituted hydrocarbon or is absent if Z=halogen;

the method comprising:
(a) linking the specific binding partner to the label; then
(b) preparing an adduct of a protective adduct former with the label so as to protect the active moiety from inactivation, from which adduct a chemiluminescent form of the label can be recovered.

7. A method as defined in claim 5 wherein the label has the formula:

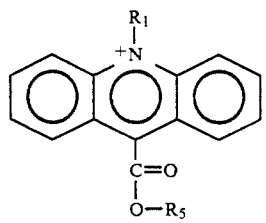

8. A method as defined in claim 6 or 7 wherein the label is linked to the specific binding partner through R$_5$.

9. A method as defined in claim 7 wherein the protective adduct former is a nucleophilic adduct former which adds at the ring 9 position.

10. A method as defined in claim 9 wherein the protective adduct former is selected from a primary thiol.

11. A method as defined in claim 10 wherein the protective adduct former is selected from a primary alkyl or aryl thiol.

12. A method as defined in claim 10 wherein the protective adduct former is selected from a primary alkyl thiol.

13. A method as defined in any one of claims 9 to 12, wherein R$_5$-Z- is selected from an optionally substituted alkoxy, alkenoxy, alkynoxy, and aryloxy.

14. A method as defined in any one of claims 9 to 12, wherein R$_5$-Z- is an optionally substituted aryloxy, and wherein R$_1$ is a substituted or unsubstituted C$_1$ to C$_5$ alkyl.

15. A labelled specific binding partner comprising:
(a) a specific binding partner;
(b) a protected label linked to the specific binding partner, the label having the formula:

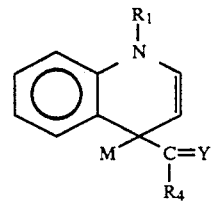

wherein the phenyl and pyridine rings are substituted or unsubstituted, and;

Y=O; N; or S;

R$_1$=H or substituted or unsubstituted hydrocarbon;

R$_4$ is a leaving group which may be linked to the specific binding partner.

is an active moiety which upon hydrolysis at the C=Y carbon yields a non-chemiluminescent form of the label, and the leaving group;

M is a protecting moiety other than H, OH, or peroxide, which is cleavable to yield deprotected, chemiluminescent label, and which is selected such that the C=Y carbon of the protected label is less susceptible to hydrolysis than in the deprotected label.

16. A labelled specific binding partner comprising:
(a) a specific binding partner;
(b) a protected label linked to the specific binding partner, the label having the formula:

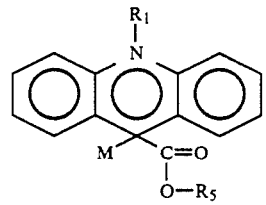

wherein the phenyl rings are unsubstituted or substituted and:

R$_1$=H or a substituted or unsubstituted hydrocarbon;

—O—R$_5$ is a leaving group in which R$_5$ may be linked to the specific binding partner;

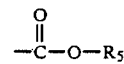

is an active moiety which upon hydrolysis at the carbonyl carbon yields a non-chemiluminescent form of the label, and the leaving group;

M is a protecting moiety other than H OH, or peroxide, which is cleavable to yield deprotected, chemiluminescent label, and which is selected such that the carbonyl carbon of the protected label is less susceptible to hydrolysis than in the deprotected label.

17. A labelled specific binding partner as defined in claim 16 wherein the deprotected label will luminesce in aqueous solution following reaction with hydrogen peroxide or oxygen, and hydroxide.

18. A labelled specific binding partner as defined in claim 16 wherein:

R₅ is substituted or unsubstituted aryl moiety; and
R¹ is an optionally substituted alkyl, alkenyl, or alkynyl moiety.

19. A labelled specific binding partner as defined in claim 18 wherein M is a primary thiol.

20. A labelled specific binding partner as defined in claim 18 wherein the two phenyl groups are substituted with a group selected from amino, substituted amino, carbonyl, hydroxyl, alkoxyl, nitro or halide substituents.

21. A labelled specific binding partner as defined in claim 25, 26, or 27 wherein $R_1$ is a $C_1$ to $C_{10}$ alkyl, and the two phenyl groups are unsubstituted.

22. A method of performing an assay for a target in a test sample, comprising:
 (a) contacting the test sample with a specific binding partner such that the specific binding partner can bind to the target, if present, the specific binding partner being linked to at least one molecule of a non-chemiluminescent protected form of a chemiluminescent label, each molecule of the protected form having, linked to the remainder of the molecule:
  (i) a labile, active moiety which is subject to inactivation to yield a non-chemiluminescent form of the label; and
  (ii) a protecting moiety which protects the active moiety from inactivation, the protecting moiety being cleavable to yield unprotected, chemiluminescent label;
 (b) deprotecting the protected label by cleaving the protecting moiety therefrom, so as to recover unprotected chemiluminescent label; and
 (c) detecting the label on the specific binding partner which may be bound to the target or on the specific binding partner which may not be bound to target, as an indication of the presence of target in the sample.

23. A method as defined in claim 22 wherein the protecting moiety is cleavable by oxidation.

24. A method as defined in claim 22 wherein the protecting moiety is cleavable by oxidation with ferricyanide.

25. A method of preparing a labelled specific binding partner, from:
 (i) a specific binding partner; and
 (ii) a chemiluminescent label having a labile, active moiety which is subject to inactivation to yield a non-chemiluminescent form of the label, and having an electrophilic site;
the method comprising:
 (a) linking the specific binding partner to the label;
 (b) preparing an adduct of a nuleophilic protective adduct former with the label at the electrophilic site thereof, which adduct former provides a protecting moiety other than H to the label, so as to protect the active moiety from inactivation, and from which adduct a chemiluminescent form of the label can be recovered.

26. A method as defined in claim 22 wherein the protected form of the chemiluminescent label has the formula:

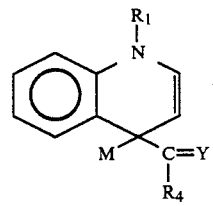

wherein the phenyl and pyridine rings are substituted or unsubstituted, and:
 Y=O; N; or S;
 $R_1$=H or substituted or unsubstituted hydrocarbon;
 $R_4$ is a leaving group may be linked to the specific binding partner.

is an active moiety which upon hydrolysis at the C=Y carbon yields a non-chemiluminescent form of the label, and the leaving group;
 M is a protecting moiety other than H, OH, or peroxide, which is cleavable to yield deprotected, chemiluminescent label, and which is selected such that the C=Y carbon of the protected label is less susceptible to hydrolysis than in the deprotected label.

27. A method as defined in claim 22 wherein the protected form of the chemiluminescent label has the formula:

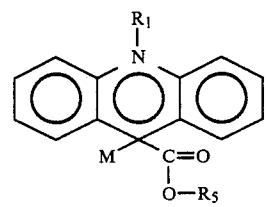

wherein the phenyl rings are substituted or unsubstituted and:
 $R_1$=H or a substituted or unsubstituted hydrocarbon;
 —O—$R_5$ is a leaving group in which $R_5$ may be linked to the specific binding partner;
 —C—O—$R_5$ is an active moiety which upon hydrolysis at the carbonyl carbon yields a non-chemiluminescent form of the label, and the leaving group;
 M is a protecting moiety other than H, OH, or peroxide, which is cleavable to yield deprotected, chemiluminescent label, and which is selected such that the carbonyl carbon of the protected label is less susceptible to hydrolysis than in the deprotected label.

28. A method as defined in claim 26 or 27 wherein the deprotected label will luminesce in aqueous solution following reaction with hydrogen peroxide or oxygen, and hydroxide.

29. A method as defined in claim 27 wherein the protected label has the following:
 R₅ is a substituted aryl or unsubstituted aryl moiety; and
 $R_1$ is a substituted or unsubstituted alkyl, alkenyl, or alkynyl moiety.

30. A method as defined in claim 29 wherein the protected chemiluminescent label has M as a primary thiol.

31. A method as defined in claim 29 wherein the protected chemiluminescent label has optional substituents on two phenyl groups which are selected from amino, substituted amino, carbonyl, hydroxyl, alkoxyl, nitro or halide substituents.

32. A method as defined in claim 28, 29, or 30 wherein, in the protected label, $R_1$ is a $C_1$ to $C_{10}$ alkyl, and the two phenyl groups are unsubstituted.

* * * * *